(12) United States Patent
Wadman

(10) Patent No.: US 7,349,096 B2
(45) Date of Patent: Mar. 25, 2008

(54) SCATTEROMETER AND A METHOD FOR OBSERVING A SURFACE

(75) Inventor: Sipke Wadman, Eindhoven (NL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 159 days.

(21) Appl. No.: 10/546,314

(22) PCT Filed: Feb. 18, 2004

(86) PCT No.: PCT/IB2004/050123

§ 371 (c)(1),
(2), (4) Date: Aug. 19, 2005

(87) PCT Pub. No.: WO2004/077032

PCT Pub. Date: Sep. 10, 2004

(65) Prior Publication Data

US 2006/0146343 A1    Jul. 6, 2006

(30) Foreign Application Priority Data

Feb. 28, 2003    (EP) ................................. 03100512

(51) Int. Cl.
*G01N 21/47* (2006.01)
*G01B 11/30* (2006.01)
(52) U.S. Cl. ...................................... 356/446; 356/600
(58) Field of Classification Search ........ 356/445–446, 356/600
See application file for complete search history.

(56) References Cited

U.S. PATENT DOCUMENTS

| | | | |
|---|---|---|---|
| 3,111,274 A | 11/1963 | Turano | |
| 4,344,709 A | 8/1982 | Provder et al. | |
| 4,575,252 A | 3/1986 | Akiyama | |
| 5,241,369 A | 8/1993 | McNeil et al. | |
| 5,595,620 A | 1/1997 | Takei | |
| 5,745,234 A | 4/1998 | Snail et al. | |
| 5,912,741 A | 6/1999 | Carter et al. | |
| 5,943,127 A | 8/1999 | Feldman et al. | |

FOREIGN PATENT DOCUMENTS

| | | |
|---|---|---|
| DE | 3731171 A1 | 3/1989 |
| DE | 19920184 C2 | 6/2001 |
| DE | 199920184 A1 | 6/2001 |
| EP | 0964244 A1 | 12/1999 |
| EP | 0964244 B1 | 12/1999 |
| GB | 470755 A | 8/1937 |
| SU | 1117496 A | 10/1984 |
| WO | WO0037923 A1 | 6/2000 |

*Primary Examiner*—Gregory J. Toatley, Jr.
*Assistant Examiner*—Amanda Merlino

(57) ABSTRACT

A scatterometer comprising light source means (11) for providing an incident light beam (8) at different angles in the direction of a sample (5) to be analyzed, and a concave screen (1,2) for receiving the reflection (19) of the incident light beam (8). The screen (1,2) has substantially the shape of a portion of a sphere, for example a hemisphere, whereby the location of the sample (5) is in its center. The screen (1,2) having an aperture (9) through which the incident light beam (8) passes towards said sample (5). Said light source means (11) and at least a portion of the screen (2) including said aperture (9) can rotate relative to the sample (5), around an axis (3) through said center and substantial perpendicular to said direction of the incident radiation beam.

8 Claims, 6 Drawing Sheets

SCATTEROMETER AND A METHOD FOR OBSERVING A SURFACE

Figure 1:
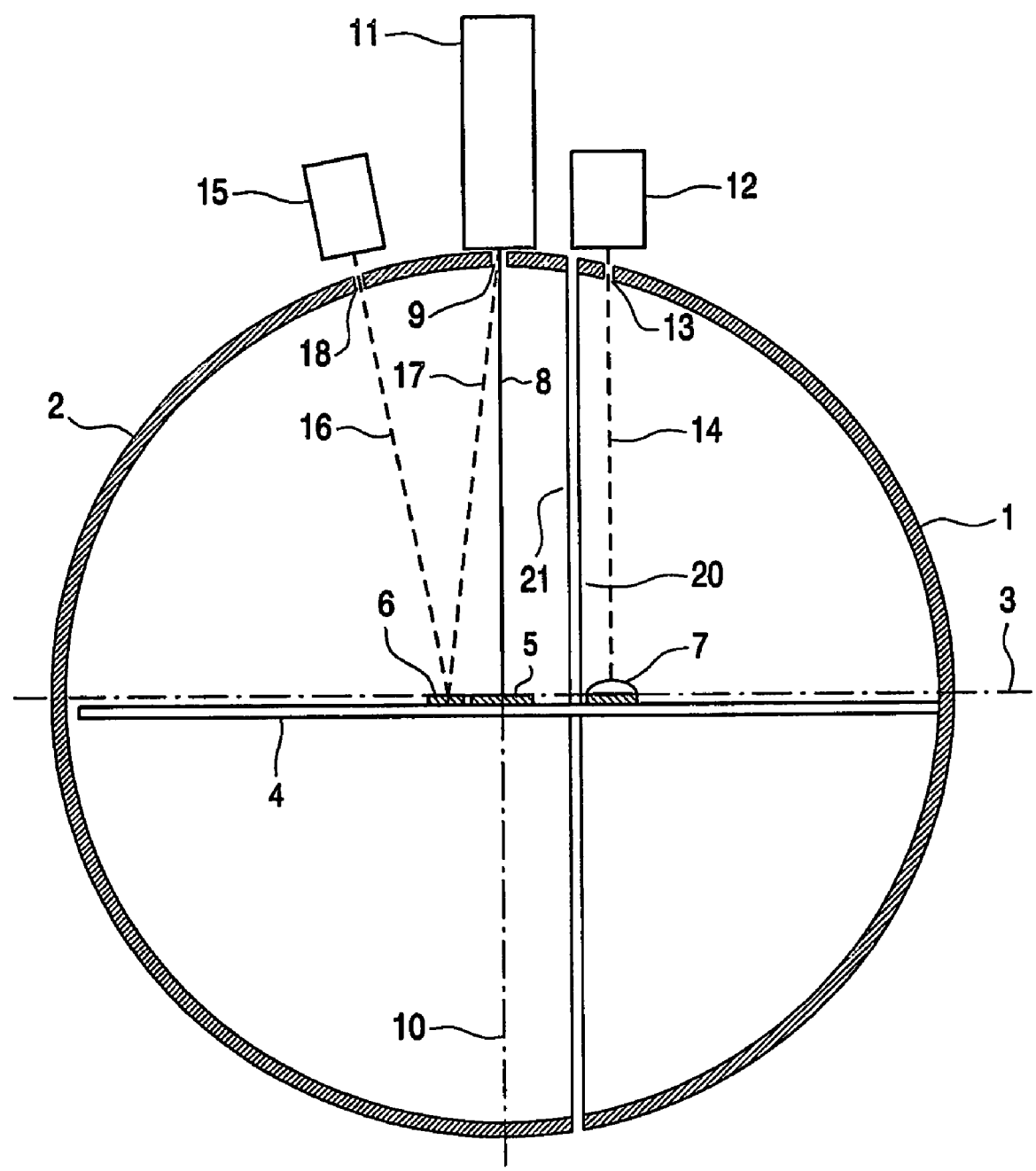

The invention is related to a scatterometer comprising light source means for providing an incident light beam at different angles in the direction of a sample to be analyzed, a concave screen for receiving the reflection of the incident light beam, the screen having substantially the shape of a portion of a sphere, the location of the sample being in its center, the screen having an aperture through which the incident light beam passes towards said sample.

Scattered light can be analyzed to provide a statistical analysis of the microstructure of a surface of a sample from which the scattered light originates. This provides a simple, non-contact, and non-perturbing monitoring technique, which is useful in many areas of technology to determine surface and subsurface morphology. In addition, the type and density of material defects, which have a geometric shape, can be characterized using this technique. Furthermore, this technique is useful for assessing the properties of coatings and materials. It is also useful in such areas as microelectronics material fabrication, optoelectronics material fabrication, optical component examination, and computer disk manufacturing.

Light scattering measurements are also useful for quality monitoring of fluids. For example, blood samples can be conveniently examined using light scattering techniques to reveal cell characteristics. Fluids with particles held in suspension, such as oils, gas containing particles, and the like can be conveniently examined using light scatter measurements. Moreover, these measurements can be made in-situ to control processes used in the manufacturing of various materials described above.

U.S. Pat. No. 5,241,369 describes a scatterometer system whereby a laser light beam incident on a sample and whereby the light scattered from the sample is received by a concave screen, thereby obtaining a two-dimensional map of a scattered light intensity pattern, and thereby characterizing the morphology of the sample in two dimensions of the spatial frequency. The near-angle scattered light, i.e. light which is scattered near the specularly reflected beam, as well as the large-angle scattered light, i.e. light which is scattered in a direction further away from the specularly reflected beam, is received by the concave screen. The screen contains one or more apertures for passing the incident light beam generated by the light source means. By making use of more apertures the light beam can be directed to the sample at different angles of incidence, whereby each aperture corresponds to a predetermined angle of incidence.

To record the image on the screen, a camera—or other detection means—may observe the screen. The camera may be directed only to the near-angle scattered light, but the camera may also observe the whole screen. In the latter case the camera can be provided with a wide-angle optical system such as a fish-eye lens or a convex mirror which may be positioned near the sample. The camera can be directed to such mirror through an aperture in the screen.

WO-A-00/37923 describes a scatterometer whereby the sample can be illuminated at many different angles of incidence, for example all angles between 0° and 90°. To that end the aperture in the screen has the shape of an elongated slit extending over up to 90° of the spherical screen. Preferably, the different incident light beams are all lying in the same so called sagittal plane of reflection, i.e. a flat plane through the sample to be analyzed, the plane containing the incident light beam and the specularly reflected beam.

However, any aperture in the screen will disturb the image of the scattered light intensity pattern. To reduce that disturbance the aperture, or the portion of an aperture that is not used for passing the incident light beam, may be covered with a material having optical properties similar to those of the remainder of the screen. Thereby the screen appears as though an aperture, or a portion of the aperture, is not present. A movable aperture cover having the same optical properties as the remainder of the screen is described in U.S. Pat. No. 5,241,369. Although such cover reduces said disturbance, in practice it has appeared that some disturbance always remain.

The object of the invention is to provide a scatterometer as described above, whereby the incident light beam can be directed at different angles of incidence to the sample, although the aperture through which the incident light beam passes the screen can be relatively small.

To accomplish with this object, said light source means and at least a portion of the screen including said aperture can rotate relative to the sample, around an axis through said center and substantial perpendicular to said direction of the incident light beam. By rotating the screen, or a portion of the screen, the aperture through which the incident light beam passes will move. Therefore it is possible to direct the incident light beam at different angles to the sample, whereby the same aperture in the screen is used. There is no need for further apertures or larger apertures to transmit the incident light beam towards the sample.

When moving (rotating) the screen with respect to the sample, different parts of the screen are used for receiving the scattered light intensity pattern. Therefore, the screen has to be larger then the image to be received. In case the image of the scattered light intensity pattern extends over a whole hemisphere around (above) the sample, then the screen should extend over a portion of a sphere, which is larger than a hemisphere.

In a preferred embodiment the portion of a sphere that is used as screen is substantially a hemisphere, whereby the whole screen is larger then a hemisphere. Therefore the screen can rotate with respect to the sample, while substantially a hemisphere shaped portion of the screen remains available as screen during such rotation. Thereby the incident light beam can hit the surface of the sample at different angles of incidence, because of the movement of the aperture in the screen, through which aperture the incident light beam approaches the sample.

Preferably, a portion of the screen can rotate and said portion is at least partially bordered by an edge forming at least a major portion of a circle in a plane perpendicular to said axis and having its center on said axis. Thereby the screen is divided in two portions forming together a part of a sphere The two portions touch each other on a seam lying on said portion of a circle, which circle is located in a plane which is parallel to the sagittal plane. One of the portions is fixed and the other portion can rotate, while the portions form together the spherical screen.

In one preferred embodiment the rotating portion of the screen forms a larger part of the hemisphere above the sample then the fixed portion of the screen, so that the sagittal plane intersects with said rotating portion of the screen. The sample as well as the aperture for passing the incident light beam is located in that sagittal plane. Preferably, the plane containing said circle (i.e. the plane in which said seam is located) is positioned at a lateral distance of between 5% and 25% of the spherical screen radius.

Preferably, the screen has an aperture through which a camera can observe the screen, or a portion of the screen, through a mirror located near the sample. In one preferred embodiment said mirror is a substantial flat mirror, and said aperture is present in the rotating portion of the screen. The mirror can be mounted in a fixed position near the sample, so that the camera keeps directed to the part of the screen where the near-angle scattered light is projected on the screen. Thereby the light source means and the camera are both rotating with the rotating portion of the screen, so that each can communicate with the inside of the spherical screen through an aperture, both apertures being present in the rotating portion of the screen.

In another preferred embodiment, or in the embodiment described above, there is a convex mirror located near the sample, whereby an aperture is present in a portion of the screen that has a fixed position with respect to the sample. A camera is directed through said aperture to said convex mirror, so that the whole hemispheric screen can be observed. In fact two cameras can be present, a first camera to record the near-angle scattered light image and a second camera recording the scattered light intensity pattern as it is projected on the hemispheric screen or a major part of it.

The invention also relates to a method for observing a surface of a sample by means of a scatterometer, whereby an incident light beam is generated by light source means and whereby said incident light beam is directed at different angles of incidence in the direction of a sample to be analyzed, whereby a concave screen receives the reflection of the incident light beam, the screen having substantially the shape of a portion of a sphere, the location of the sample being in its center, the screen having an aperture through which the incident light beam passes towards said sample, whereby said light source means and at least a portion of the screen including said aperture rotate relative to the sample, around an axis through said center and substantial perpendicular to said direction of the incident light beam.

Figure 2:
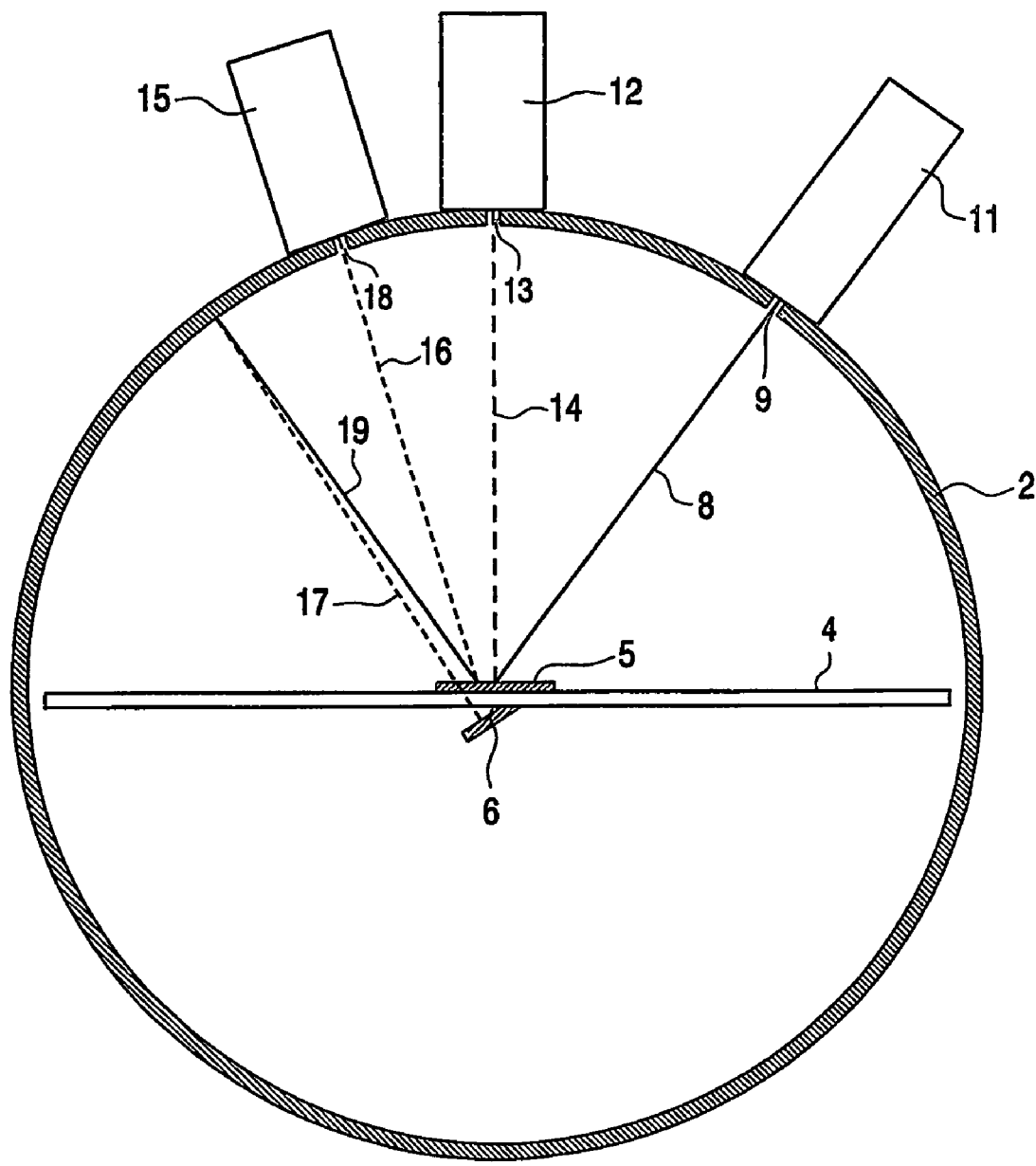
Figure 3:
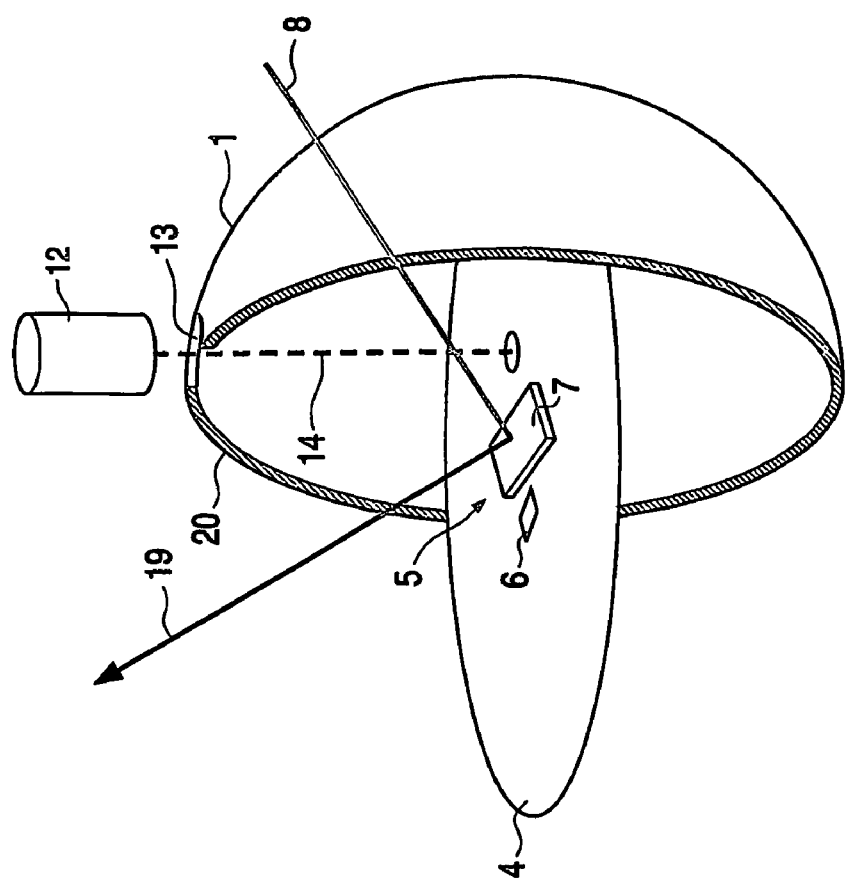
Figure 3:
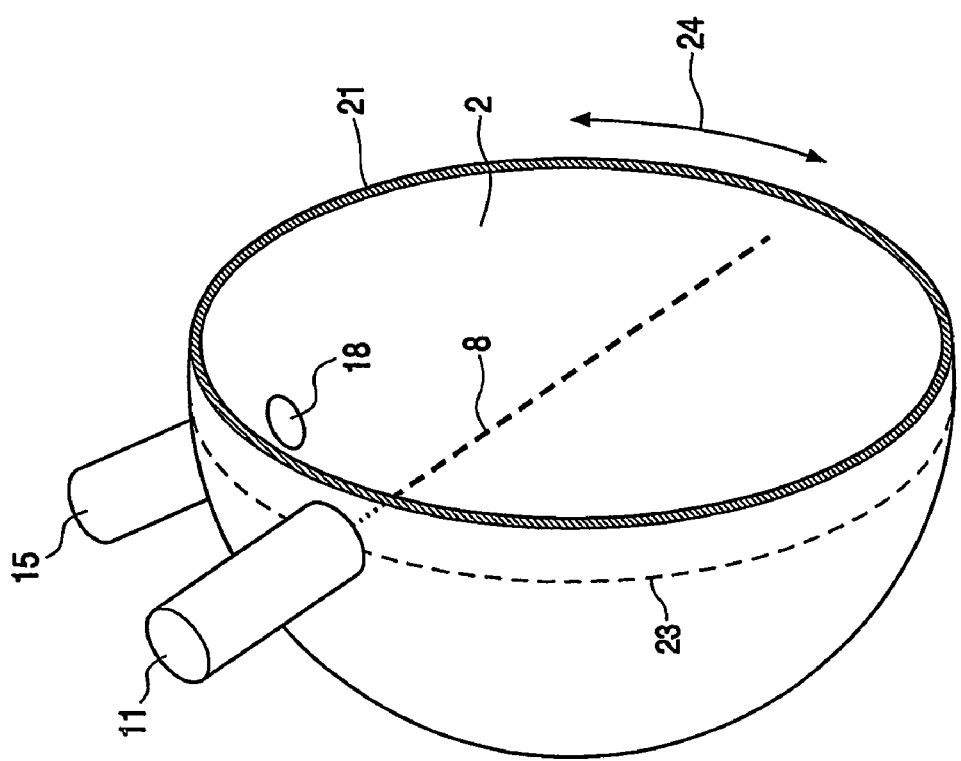
Figure 4:
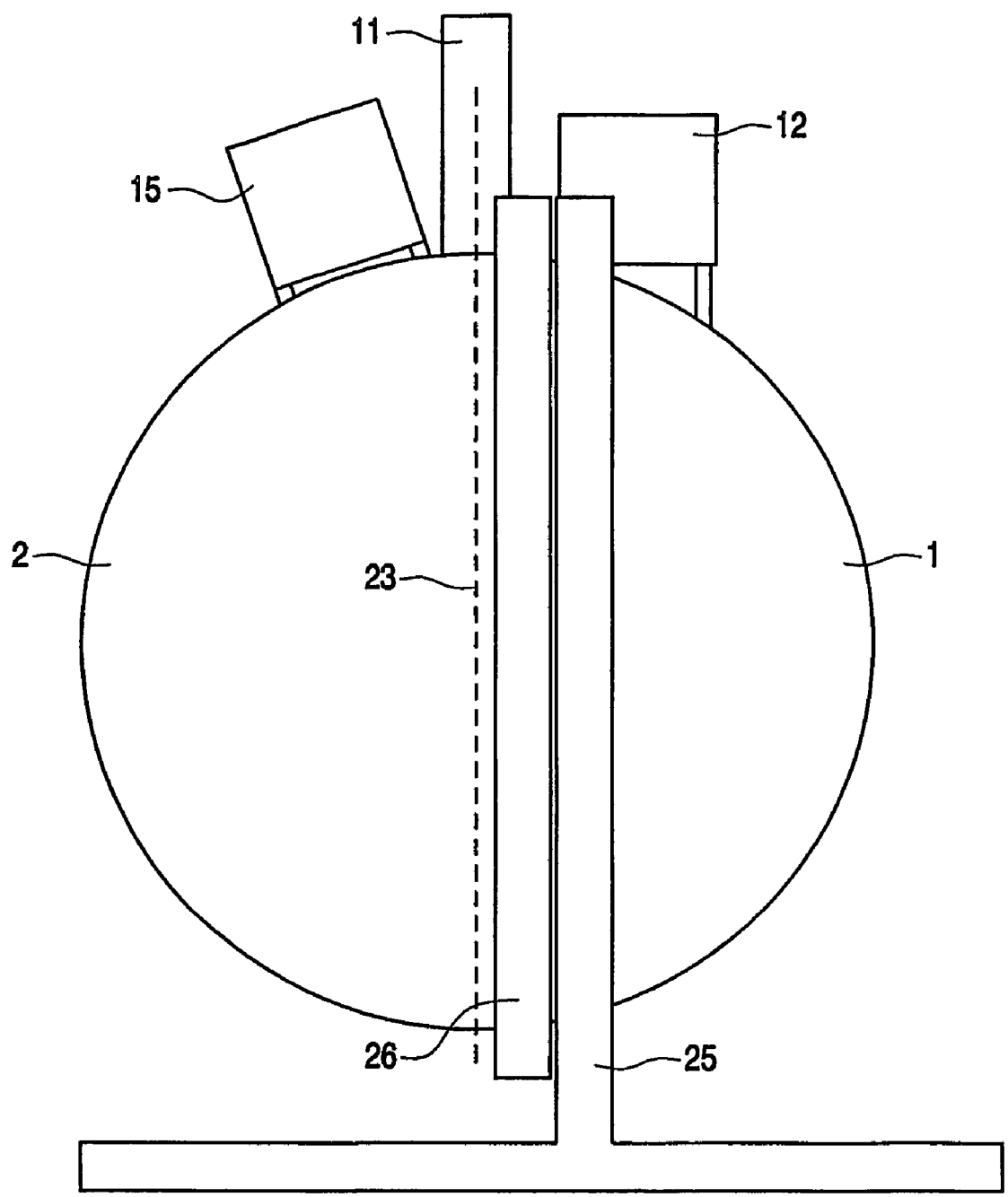
Figure 5:
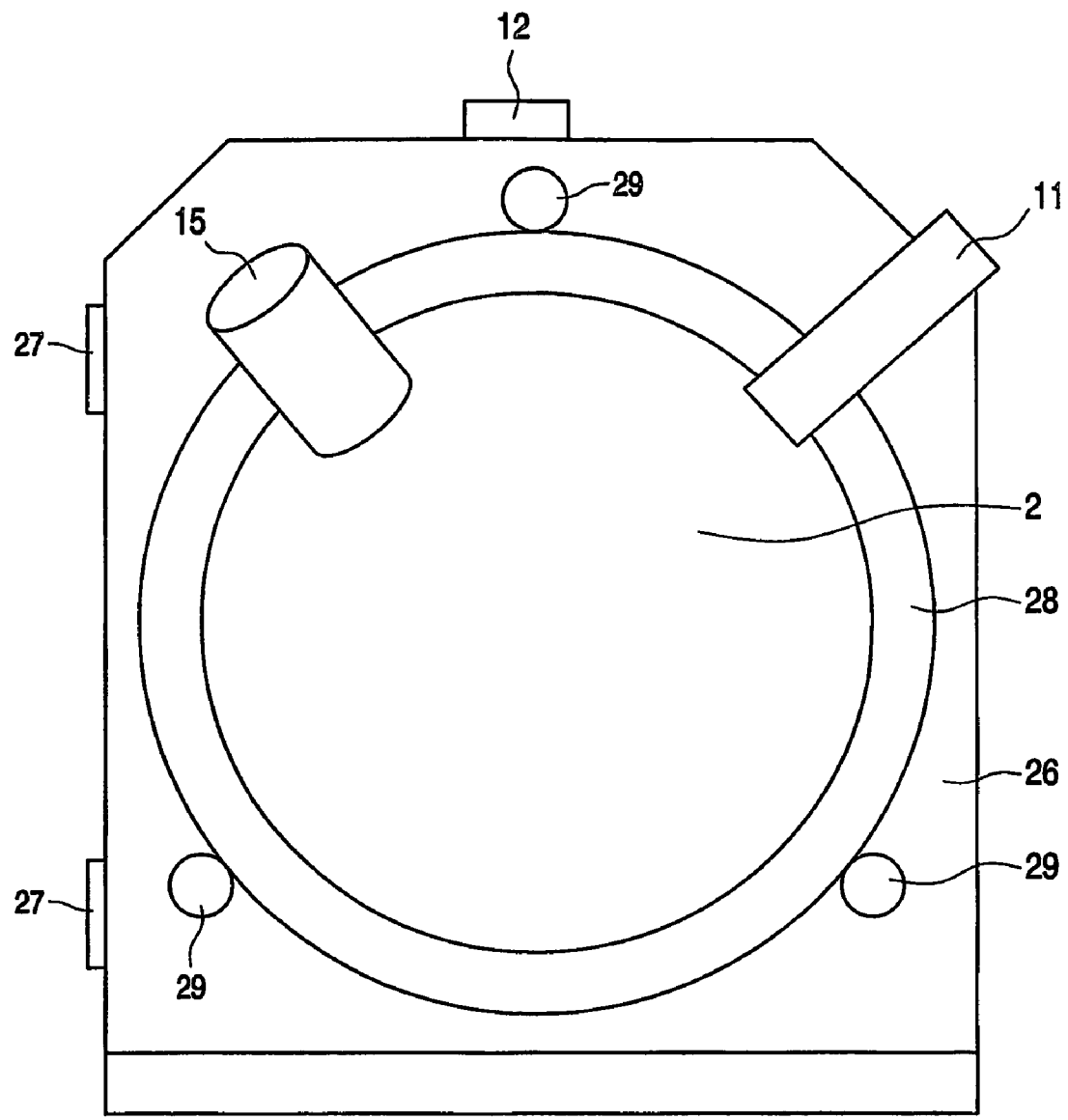
Figure 6:
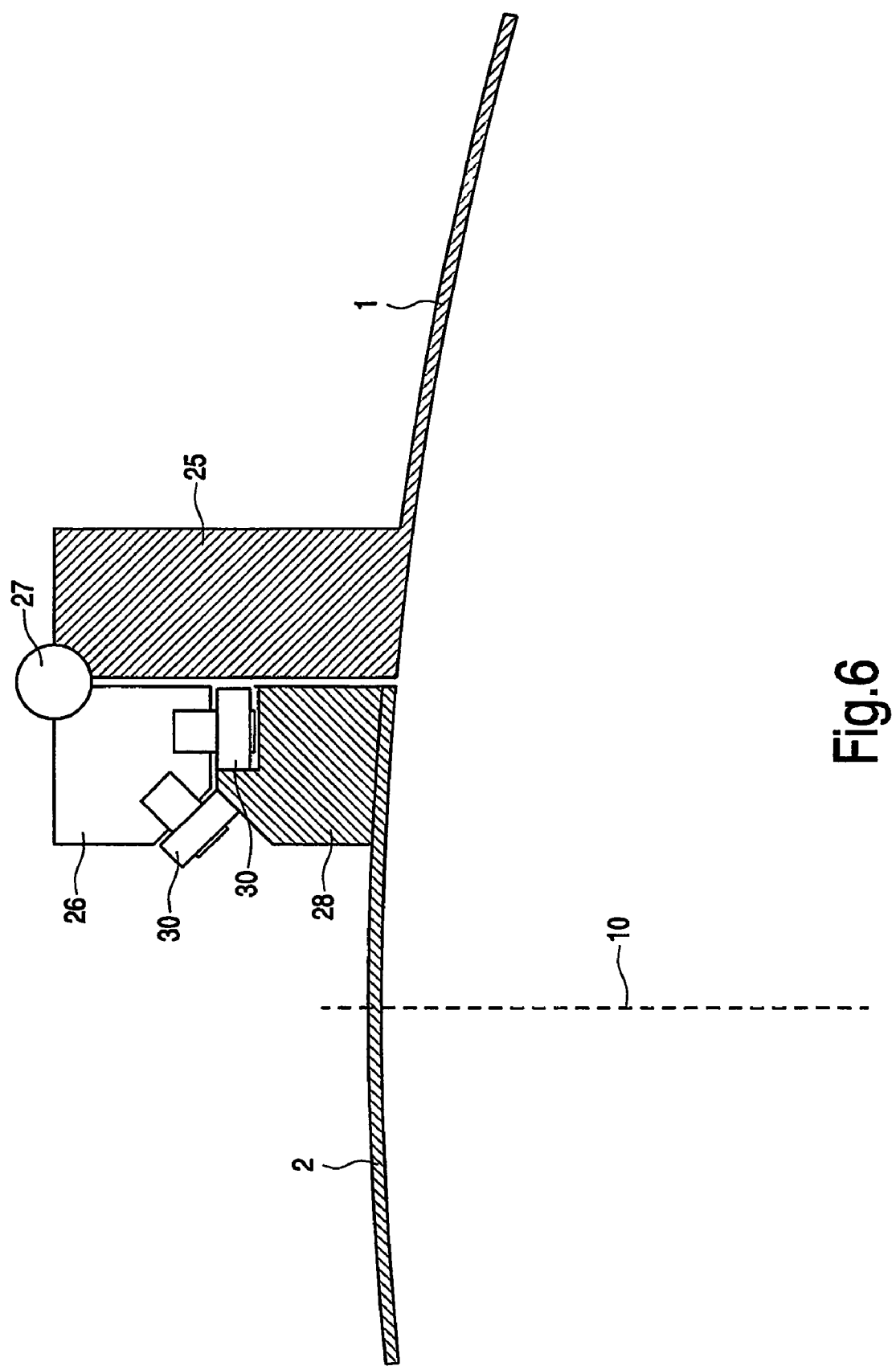

The invention will now be explained by means of a description of an embodiment of a scatterometer, in which reference is made to a drawing, in which:

FIG. 1 is a sectional view in a vertical plane;
FIG. 2 is a sectional view in another vertical plane;
FIG. 3 is a perspective view;
FIG. 4 is a front view of the scatterometer;
FIG. 5 is a side view of the scatterometer; and
FIG. 6 shows a guiding assembly.

The figures are only schematic representations of the embodiment. To explain the working principle, only some parts of the scatterometer are schematically shown, other parts are not shown.

According to FIG. 1, the scatterometer comprises a screen composed of two portions 1,2. The two portions 1,2 form together a sphere, and the upper part (upper hemisphere) of the concave internal surface of that sphere is the screen on which the scattered light intensity pattern is projected. The right portion 1 of the sphere extends over less than a hemisphere and it has a fixed position. The left portion 2 extends over more than a hemisphere and it can rotate around axis 3, lying in the plane of the drawing.

Inside the sphere 1,2 there is a base plate 4. Base plate 4 has a fixed position and is attached to fixed portion 1 of the sphere. A sample 5, having a surface to be analyzed, is attached to the base plate, so that it is located in the center of the sphere 1,2, whereby its surface coincide with the axis of rotation 3. A flat mirror 6 and also a convex mirror 7 are mounted on the base plate 4 near sample 5.

Light source means 11 are attached to the backside of the rotating portion 2 of the screen. The light source means 11 generate an incident light beam 8, which is directed to the sample 5 through an aperture 9 in screen 2. The incident light beam 8 coincides with the sagittal plane, which plane is positioned perpendicular with respect to the plane of FIG. 1 and is indicated with dotted line 10.

A first camera 12 is attached to the backside of the fixed portion 1 of the screen. First camera 12 is directed to the convex mirror 7 through an aperture 13 in portion 1 of the screen, as indicated by striped line 14. Because mirror 7 is convex, first camera 12 can observe and record the whole screen extending over the upper hemisphere.

A second camera 15 is attached to the backside of the rotating portion 2 of the screen. Second camera 15 is directed to the flat mirror 6 through an aperture 18 in portion 2 of the screen, as indicated with striped line 16. Mirror 6 is fixed in such position that the second camera observes a part of the screen near the sagittal plane 10, as indicated by striped line 17.

Each of the two portions 1,2 of the sphere is bounded by an edge 20,21, each forming a circle with the same diameter. The two edges 20,21 are positioned close to each other, so that the "seam", formed by the two edges 20,21, does not disturb the image on the screen. In FIG. 1 the two edges 20,21 are spaced apart, but in practice they will touch or almost touch each other, so that on the screen the seam is almost invisible.

In FIG. 1, the light source means 11 and the second camera 15 are both located on top of the upper hemisphere, to show them clearly. However, in fact both elements 11,15 has another position, as is shown in FIGS. 2, 3 and 5.

FIG. 2 shows schematically a sectional view of the scatterometer, whereby the sagittal plane 10 (see FIG. 1) is the plane of the drawing. The rotating portion 2 of the screen is rotated to a position in which the incident light beam 8 hits the surface of the sample 5 at a certain angle. The reflection of the incident light beam 8 comprises near-angle scattered light and large-angle scattered light. The near-angle scattered light forms a reflected radiation beam 19, and the large-angle scattered light is projected over the whole, or a major part, of the screen formed by the internal surface of the upper hemisphere. Both reflections, the near-angle scattered light and the large angle scattered light, are observed and recorded by the two cameras 12,15.

First camera 12 records the large-angle scattered light as it is projected on the screen formed by the upper hemisphere of the two portions 1,2 of the screen. Thereby the camera 12 is directed to the convex mirror 7 (FIG. 1). Because camera 12 and mirror 7 have both a fixed position, together with portion 1 of the screen, always the upper hemisphere will be observed by camera 12.

Second camera 15 records the image formed by the near-angle scattered light on the screen, by observing the screen through flat mirror 6. Flat mirror 6 has a fixed position on the base plate 4, and second camera 15 is attached to rotating portion 2 of the screen. Because the light source means 11 are also attached to the rotating portion 2 of the screen, they will move together with second camera 15 and therefore second camera 15 will automatically be directed to the image of the near angle scattered light at each position of rotating portion 2 of the screen, which will be clear from FIG. 2.

FIG. 3 is a schematic perspective view of the described embodiment of the scatterometer, whereby the portions 1,2 of the screen are taken apart from each other. The light source means 11 and the second camera 15 are attached to the rotating portion 2 of the screen. In that rotating portion 2 the intersection with the sagittal plane is indicated with striped line 23 and the rotation is indicated with arrow 24.

In the operating position of the scatterometer, the circular edge 21 of the rotating portion 2 is close to the circular edge 20 of the fixed portion 1, so that an almost uninterrupted screen is achieved.

FIG. 3 shows furthermore fixed portion 1 of the screen and first camera 12 attached to it. Aperture 13 allows first camera 12 to be directed to convex mirror 7 on the base plate 4. Base plate 4 is attached to fixed portion 1 of the screen and therefore also in a fixed position. Sample 5 and flat mirror 6 are also present on base plate 4.

FIG. 4 is a view of the scatterometer in the operational position, whereby, just as in FIG. 1, the light source means 11 and the second camera 15 are shown on top of the upper hemisphere to show them clearly. As shown in FIG. 4, fixed portion 1 of the screen is mounted in fixed frame 25. Rotating portion 2 of the screen is connected to a hinging frame 26, in which hinging frame 26 the rotating portion 2 can rotate. The sagittal plane is indicated with the striped line 23.

FIG. 5 is also a view of the scatterometer in operational position, seen from the left side compared to FIG. 4. Just like in FIGS. 2 and 3, the light source means 11 and the second camera 15 are both shown in their correct locations on the rotating portion 2 of the screen. The hinging frame 26 is attached to fixed frame 25 by two hinges 27. In the operational position, as shown in FIG. 5, the fixed frame 25 and the hinging frame 26 are locked together by locking means (not shown in the figure). The hinging frame carries a rotating ring 28, which ring 28 is attached to the rotating portion 2 of the screen. Rotating ring 28 is supported in hinging frame 26 by three guiding assemblies 29, in FIG. 5 indicated as circles.

FIG. 6 shows a guiding assembly 29 schematically, but in more detail. Fixed frame 25 is attached to the fixed portion 1 of the screen. Hinging frame 26 is connected through hinges 27 with the fixed frame 25. Rotating portion 2 of the screen is attached to ring 28, which ring 28 can rotate in hinging frame 26. The rotating movement of ring 28 is guided by three guiding assemblies 29 (see FIG. 5), each comprising two guiding wheels 30. Guiding wheels 30 are attached to hinging frame 26 and engage ring 28, as is shown in FIG. 6.

It will be clear that in the operational position the surface of the sample 5 can be hit by the incident light beam at different angles, depending on the rotational position of portion 2 of the screen. Thereby the scattered light will project a light intensity pattern on the screen formed by the upper hemisphere of the adjacent portions 1 and 2 of the screen. Said pattern can be recorded by first camera 12 though a convex mirror 7. The near-angle scattered light can be recorded by second camera 15 though flat mirror 6.

The three apertures 9,13,18 in the screen can be held small and because of the rotation of portion 2 of the screen, there is no need for larger or more apertures to enable the use of different angles at which the surface of the sample 5 is hit by the incident light beam.

The described embodiment of the scatterometer is merely an example; a great many other embodiments are possible.

The invention claimed is:

1. A scatterometer comprising light source means for providing an incident light beam at different angles in the direction of a sample to be analyzed, a concave screen for receiving the reflection of the incident light beam, the screen having substantially the shape of a portion of a sphere, the location of the sample being in its center, the screen having an aperture through which the incident light beam passes towards said sample, characterized in that said light source means and at least a portion of the screen including said aperture can rotate relative to the sample, around an axis through said center and substantial perpendicular to said direction of the incident radiation beam.

2. A scatterometer as claimed in claim 1, characterized in that said portion of a sphere is substantially a hemisphere.

3. A scatterometer as claimed in claim 1,characterized in that a portion of the screen can rotate and said portion is at least partially bordered by an edge forming at least a major portion of a circle in a plane perpendicular to said axis and having its center on said axis.

4. A scatterometer as claimed in claim 3, characterized in that said plane is positioned at a lateral distance of between 5% and 25% of the spherical screen radius.

5. A scatterometer as claimed in claim 1, characterized in that the screen has an aperture through which a camera can observe the screen, or a portion of the screen, through a mirror located, near the sample.

6. A scatterometer as claimed in claim 5, characterized in that said mirror is a substantial flat mirror, and in that said aperture is present in the said at least portion of the screen that can rotate relative to the sample.

7. A scatterometer as claimed in claim 5, characterized in that said mirror is a convex mirror, and in that said aperture is present in a portion of the screen that has a fixed position with respect to the sample.

8. A method for observing a surface by means of a scatterometer, whereby an incident light beam is generated by light source means and whereby said incident light beam is directed at different angles of incident in the direction of a sample to be analyzed, whereby a concave screen receives the reflection of the incident light beam, the screen having substantially the shape of a portion of a sphere, the location of the sample being in its center, the screen having an aperture through which the incident light beam passes towards said sample, characterized in that said light source means and at least a portion of the screen including said aperture rotate relative to the sample, around an axis through said center and substantial perpendicular to said direction of the incident light beam.

* * * * *